United States Patent [19]
Wyatt et al.

[11] Patent Number: 5,530,540
[45] Date of Patent: Jun. 25, 1996

[54] LIGHT SCATTERING MEASUREMENT CELL FOR VERY SMALL VOLUMES

[75] Inventors: Philip J. Wyatt; Gary R. Janik, both of Santa Barbara, Calif.

[73] Assignee: Wyatt Technology Corporation, Santa Barbara, Calif.

[21] Appl. No.: 285,367

[22] Filed: Aug. 3, 1994

[51] Int. Cl.⁶ ................................................. G01N 21/05
[52] U.S. Cl. ............................ 356/246; 356/338; 356/343
[58] Field of Search ............................... 356/73, 246, 336, 356/338, 339, 342, 343, 440, 39; 250/573, 574, 576

[56] References Cited

U.S. PATENT DOCUMENTS

| 4,352,558 | 10/1982 | Eisert | 356/73 |
| 4,440,497 | 4/1984 | Carey et al. | 356/246 |
| 4,515,274 | 5/1985 | Hollinger et al. | 356/246 |
| 4,673,289 | 6/1987 | Gaucher | 356/246 |
| 5,030,002 | 7/1991 | North, Jr. | 356/73 |
| 5,138,181 | 8/1992 | Lefevre | 356/246 |

*Primary Examiner*—Richard A. Rosenberger
*Attorney, Agent, or Firm*—Philip J. Wyatt

[57] ABSTRACT

A modified light scattering cell, and associated method, whereby an eluant of very small dimension transverse to its direction of flow is entrained successively by two sheath flows and presented to a fine light beam that illuminates the entrained eluant as it flows through the light beam. The light scattered by the entrained eluant is collected by detectors outside of a transparent flow cell enveloping the sheath flow entrained eluant. The windows of the transparent flow cell through which the light beam enters and leaves are far removed from the scattering eluant and kept clear of eluant-contained particles by means of flow components that will form subsequently one of the eluant sheath flows employed. The eluant source is typically from a fine capillary such as found in capillary electrophoresis, capillary hydrodynamic fractionation, and flow cytometry applications.

17 Claims, 9 Drawing Sheets

LIGHT SCATTERING MEASUREMENT CELL FOR VERY SMALL VOLUMES

This patent relates to the measurement of the scattered light intensifies from particles entrained within very small volumes of fluid. Many of the consequences of such measurements and some preferred embodiments for achieving them have been developed in the following related U.S. patents and co-pending application together with their many foreign derivatives:

PATENTS

U.S. Pat. No. 4,541,719 Title: Method and apparatus for characterizing microparticles and measuring their response to their environment Inventor: P. J. Wyatt Date of Filing: Jul. 20, 1982 Date of Issue: Sep. 17, 1985 Art Unit No: 255

Des. U.S. Pat. No. 329,821 Title: Apparatus for the measurement of fine particles in liquid suspension by the light scattering procedure. Inventors: P. J. Wyatt and R. F. Shuck Date of Filing: Feb. 21, 1989 Date of Issue: Sep. 29, 1992 Art Unit No: 291

U.S. Pat. No. 4,616,927 Title: Sample cell for light scattering measurements Inventors: S. D. Phillips, J. M. Reece and P. J. Wyatt Date of Filing: Nov. 15, 1984 Date of Issue: Oct. 14, 1986 Art Unit No.: 255

U.S. Pat. No. 4,710,025 Title: Process for characterizing suspensions of small particles Inventors: P. J. Wyatt and G. M. Quist Date of Filing: Sep. 9, 1985 Date of Issue: Dec. 1, 1987 Art Unit No.: 255

U.S. Pat. No. 4,907,884 Title: Sample cell monitoring system Inventors: P. J. Wyatt and S. D. Phillips Date of Filing: Jun. 5, 1987 Date of Issue,: Mar. 13, 1990 Art Unit No.: 255

U.S. Pat. No. 5,129,723 Title: High performance Zimm chromatography—HPZC Inventors: J. Howie, C. Jackson and P. J. Wyatt Date of Filing: Apr. 11, 1991 Date of Issue: Jul. 14, 1992 Art Unit No.: 255

U.S. Pat. No. 5,404,217 Title: Laser liquid flow cell manifold Inventors: G. R. Janik and J. F. Magolske Date of Filing: Aug. 26, 1993 Date of Issue: Apr. 4, 1995 Art Unit Number: 2605

BACKGROUND

Among the patents referenced above, the scattering cell described in U.S. Pat. No. 4,616,927, hereinafter referred to as the 927 flow cell or some of its slight modifications as shown in U.S. Pat. No. 5,404,217, hereinafter referred to as the 217 flow cell, has proven to be particularly useful for measuring the variation of scattered light intensity with scattering angle from particles in solution illuminated with a free light beam, such as produced by a laser. The term "particles" refers quite generally to the range of objects from macromolecules at the one extreme to large mammalian cells or even phytoplankton at the other. Characteristically, macromolecules whose molecular weights may be determined from their light scattering properties are of the order of 1000 gms/mol up to tens of millions of grams per mol. Their physical extent or size may vary from one nanometer to tens of micrometers. Prior to measuring the light scattered by the illuminated particles, it is very often desirable to separate them by chromatographic means such as size exclusion chromatography, or reverse phase chromatography. Connected on-line to such a chromatographic system and immediately following the separation columns, the 927 or 217 flow cell incorporated in a read head surrounded by an array of detectors provides a useful means for measuring the scattered light intensity from the separated sample flowing therethrough. From these measurements, the molecular weight and size distributions of the separated molecules may be determined following the standard techniques associated with these measurements. A detailed review and explanation of these methods, and how as they relate to the 927 flow cell, may be found in the 1993 article by P. J. Wyatt in Analytica Chemica Acta, volume 272, pages 1–40.

The 927 flow cell has been modified somewhat since its associated patent issued by changing its bore ends slightly and enclosing it into an integrated manifold structure such as disclosed in Design U.S. Pat. No. 329,821 by Wyatt and Shuck or, more recently, as disclosed in U.S. Pat. No. 5,404,217 by Janik and Magolske. Despite the many advantages of this type of flow cell for performing light scattering measurements on flowing samples following chromatographic separation, there are certain types of separations that produce exceptional sample resolution, yet function only for very small quantities of material. For example, when particles are separated by means of capillary hydrodynamic chromatography, or CHDF, as described, for example, in the article by Silebi and Dos Ramos in the Journal of Colloid and Interface Science, volume 130, pages 14 to 24, the capillary diameter is typically 60 μm or less. The total sample volume injected into such a capillary would be of the order of 0.05 μl. In order to measure the light scattering properties of this subsequently fractionated sample using the cell of the aforereferenced patents and co-pending application, the sample would have to be diluted by the square of the ratio of the flow cell bore diameter to the capillary diameter, or $(1.25 \text{ mm}/5\times10^{-2} \text{ mm})^2 = 625$, since the flow cell bore is typically of the order of 1.25 mm. At this level of dilution after fractionation, not even considering the fractionation stage itself, which may dilute the injected volume by an order of magnitude or more, many fractionated samples will produce very low light scattering, hereinafter referred to by LS, signals or be undetectable. Indeed, the mismatch of flow channel diameters has appeared to be a major impediment to using the 927 flow cell to make light scattering measurements for samples eluting from such capillaries. Such huge volume dilutions have affected also the practicality of using refractive index detectors, with separations such as CHDF or capillary electrophoresis hereinafter referred to by CE. The similar small sample volume problems associated with CE are discussed, for example by Weinberger in his book Practical Capillary Electrophoresis.

Flow cytometry, hereinafter referred to as FC, represents another important area for the application of LS measurements. Because the illuminating laser sources are generally tightly focused, such as in the FC instruments manufactured for example, by Becton-Dickenson, Miles Laboratories, Ortho Diagnostics, or Coulter Electronics, it is particularly important to insure that the individual cells flow in a highly collimated and confined manner, as well. This type of flow constraint requirement is illustrated, for example, in U.S. Pat. No. 3,785,735 by Friedman et al. wherein is described a fine capillary based flow cell. Although some light scattering measurements are achieved by their design, the omnipresence of the various glass-liquid interfaces preclude great flexibility for making such measurements over a broad range of scattering angles. The design of the Friedman et al. flow cell insures very tight transverse control of the flowing particles by creating converging sheath flows all of which entrain the particles forcing them to flow through a fine capillary drilled into a larger glass structure. Once within the capillary itself, the entrained particles are expected to remain centered because of the occurance of laminar flow conditions. The main purpose of the sheath flow elements is to dilute and transport the particles into the narrow capillary in which they will be examined. The possibility that transverse spatial confinement could be achieved without the need for a stationary transparent capillary was not utilized by Friedman et al. nor to the designers of many types of so-called flow cytometers, including the types manufactured by the aforereferenced Coulter Electronics and Becton Dickenson companies.

In 1953, Crosland-Taylor reported in vol. 171 of Nature, pp 37–38, a new means for counting small particles. In this article he pointed out that narrow tubes, or capillaries, make "... microscopial observation of the contents of the tube[s] difficult due to the different refractive indices of the tube and the suspending fluid ... " He also noted that such narrow tubes tend to block easily. Thus began his explanation of a device comprised of a relatively large tube through which flowed a stream of sheath-entrained particles. He described the sheath concept as comprised of the slow injection of a particle suspension into a faster stream of fluid flowing in the same direction. The faster sheath stream is, in turn, comprised of two sources from opposite sides of the injected sample. The two sources are needed to insure that the injected sample stream remains centered. For the Crosland-Taylor structure, particles are examined in regions where the diameter of the stream is the greatest. The particles are at a relatively great distance from the walls of the flow cell. For capillary-centered cells, on the other hand, the particles are very close to the flow cell boundaries. Conventional, flow cytometers of the types described earlier invariably rely on laminar flow containment and capillary flow cells of very small radius.

Microbore chromatography, a variant of liquid chromatography, is a separation technique which also involves the use of very small sample and solvent volumes. A sheath flow cell, of a simpler design than that of Crosland-Taylor used for detecting laser fluorescence in microbore chromatography has been reported by Hershberger, Callis, and Christian in Analytical Chemistry, volume 51, pages 1444 to 1446. Although the sample diameter and volume were as low as 0.05 mm and 6 μl, respectively, the distance between the liquid/glass interfaces was about 10 mm, much larger than for flow cells used in the commercial flow cytometers discussed earlier. In this design, however, the liquid near the interfaces is essentially stationary and a single sheath contribution is provided by means of a flow within a tube concentric with the column exit flow stream.

The present invention, while providing a means for utilizing the 927 or 217 flow cell and avoiding the associated dilution problems, also presents a more general formulation for making light scattering measurements from a tightly confined sample.

SUMMARY OF THE INVENTION

Figure 5:
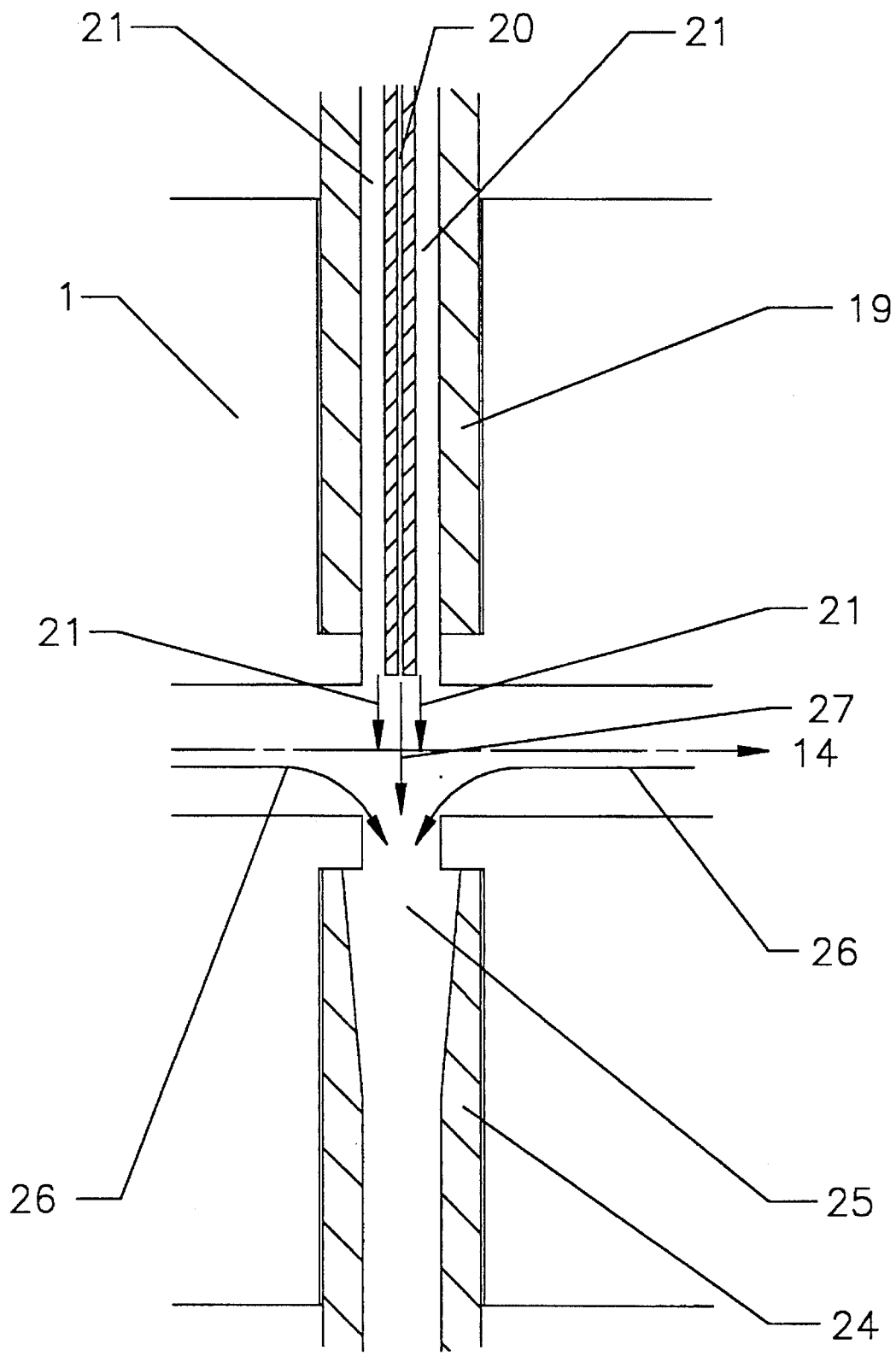
FIG. 5 shows details of the combining flows that make up the sheath flow by means of a cross sectional view of a plane through the transverse holes of FIG. 3 but in a plane orthogonal to that shown in FIG. 4, i.e., including the axis of the main bore.

Samples separated within a capillary or other small bore structure are entrained by laminar flow upon leaving the capillary to remain confined to a very small volume centered on an axis perpendicular to the axis of light beam passing through the flow cell, at its center, as shown in FIG. 5. It is the purpose of the entraining laminar flow to retain to the fullest extent possible the spatial separation achieved within the capillary itself. In addition, a further object of the invention is to maintain the eluting fractions with minimal dilution during their passage through the illuminating light beam. Another objective of the invention is to preserve the refractive properties of the 927 or 217 flow cell that permit the measurement of scattered light from separated samples illuminated within the cell. In order to achieve these objectives, a laminar flow from three sources is created about the fractions as they leave the capillary or are otherwise introduced into the LS region.

For a more general LS environment wherein it is necessary to maintain the scattering particles within a tightly controlled flowing region, while at the same time minimizing stray light, a more general flow cell structure is presented.

DETAILED DESCRIPTION OF THE INVENTION

Figure 1:
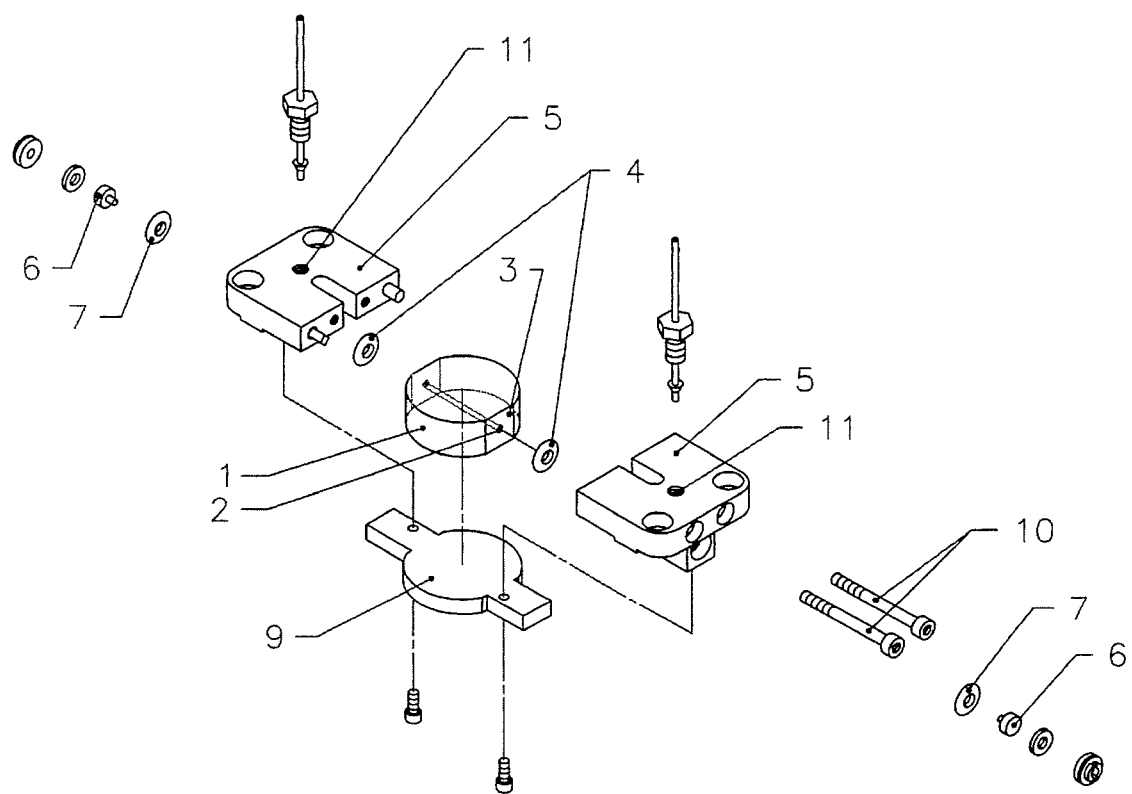
FIG. 1 shows the structure of the 217 flow cell as currently implemented with manifolds and fixtures.
Figure 2:
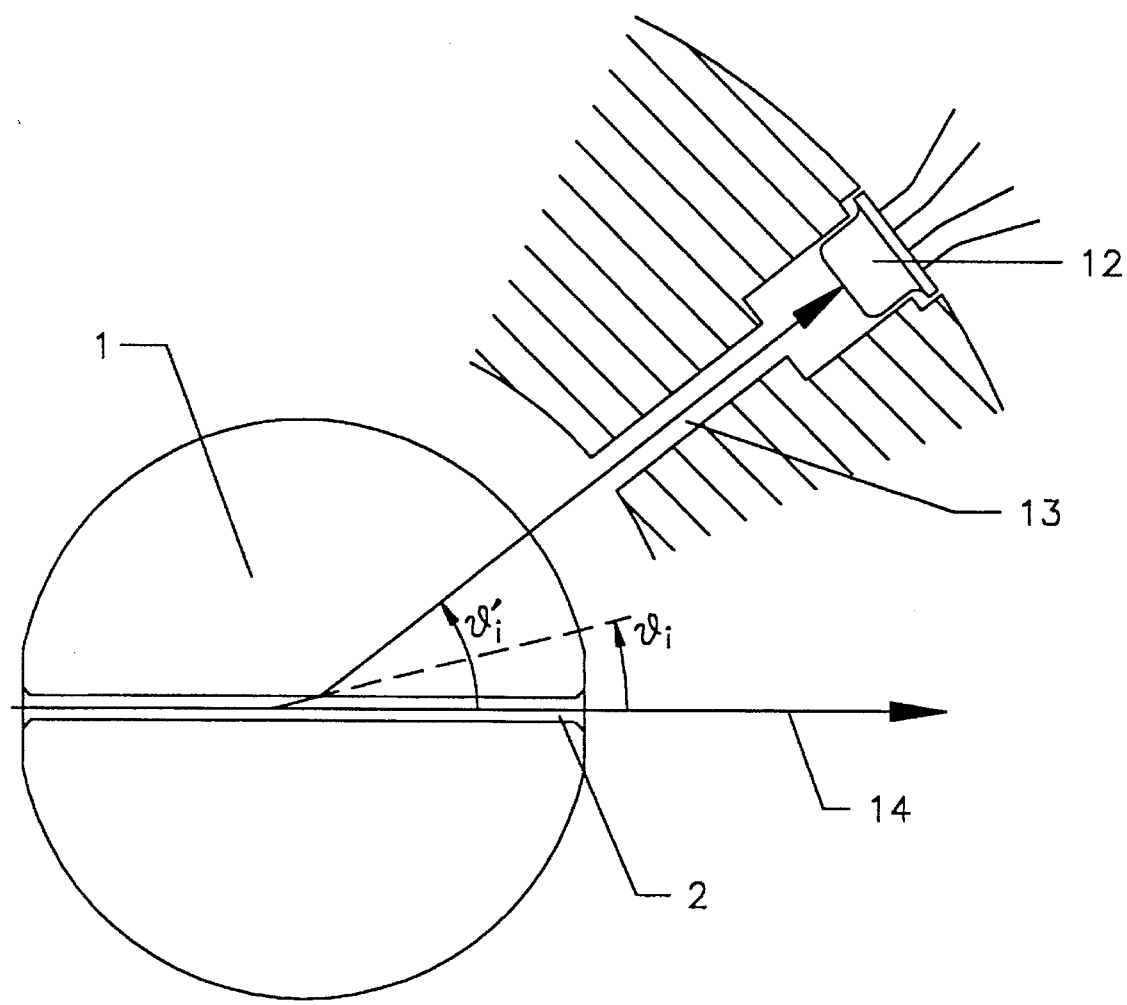
FIG. 2 shows the refractions of light scattered within the 927 or 217 flow cell.

The 927 or 217 flow cell has been shown to be a particularly useful structure for the measurement of light scattered from samples separated by liquid chromatographic means such as size exclusion chromatography or reverse phase chromatography. This flow cell has been utilized extensively in commercially distributed light scattering photometers such as the DAWN® and miniDAWN instruments manufactured by Wyatt Technology Corporation of Santa Barbara, Calif. FIG. 1 shows an exploded view of the 217 flow cell with all of the associated manifold and optical fixtures of the aforereferenced design patent, to permit an intended implementation of the cell within a light scattering photometer of the DAWN type, previously mentioned. The cell 1 is a section of a right cylinder made of glass of refractive index $n_g$ with a bore 2 through a diameter perpendicular to flattened ends 3. These ends are mated by seals 4 to manifolds 5 holding windows 6 retained by rings 7 and associated seals 8 which fit between retaining manifolds 5 and windows 6. The bottom retaining plate 9 together with assembly bolts 10 complete the structure. Threaded apertures for chromatographic or other fittings 11 permit the liquid samples to flow into and out of the structure. In its preferred embodiment, the sample flows through the cell bore 2 whose diameter is of the order of 1.25 mm. Collinear with this flow and lying along its central axis is a fine light beam, such as produced by a laser, which enters through one of the windows 6 shown and exits through the other. The windows of this type of cell embodiment provide transparent interface means which separate the liquids within the cell from the generally air regions exterior in which are mounted scattered light detectors. The assembled structure is surrounded at the curved glass cell surfaces by an array of detectors coplanar with the bore 2 and set at fixed angles $\theta_i'$ as illustrated for a single detector in FIG. 2. Each detector 12 is generally collimated by collimation means 13 and collects light scattered into scattering angle $\theta_i$ by the particles carried by the solvent illuminated by the light beam 14. The scattered light is refracted at the solvent/glass boundary into fixed angle $\theta_i'$. The fixed angles $\theta_i'$ are related to the scattering angles $\theta_i$ by Snell's Law to yield $$n_g \cos \theta_i' = n_s \cos \theta_i, \quad (1)$$

where $n_s$ is the refractive index of the solvent transporting the particle sample through the cell bore 2 and threaded fluid entry and exit fittings 11. The refractions indicated by Eq. (1) are shown in FIG. 2 wherein the light beam 14 is shown passing through the particle bearing solvent flowing within the bore 2.

A major advantage of the aforementioned implementation of the 927 or 217 flow cell is that the windows 6, through which the fine light beam passes, are well outside the field of view of any of the detectors 12. It is well known by those skilled in the art of light scattering measurements that the air/glass and liquid/glass interfaces through which the illuminating light beam enters and exits are invariably the source of stray light due to a natural tendency of such beams to scatter and generate stray light whenever any impurities or imperfections exist on the interface surfaces. All such surfaces are always potential loci for precipitation which, in turn, can cause beam flarings. For separations such as CE and CHDF, measurement of the angular variation of scattered light from within the capillary itself becomes particularly difficult because the region surrounding the samples are generally cylindrical with a radius of only 25 μm or less. The flare problems associated with attempting to enclose such flow in a cylindrical structure of such a small radius are essentially unmanageable. It thus appears reasonable to try to enclose the eluant leaving the separation capillary with a sheath flow of fluid with the same index of refraction that would preserve the spatial separations of the sample obtained within or before the capillary, yet produce negligible dilution and stray light effects.

Figure 3:
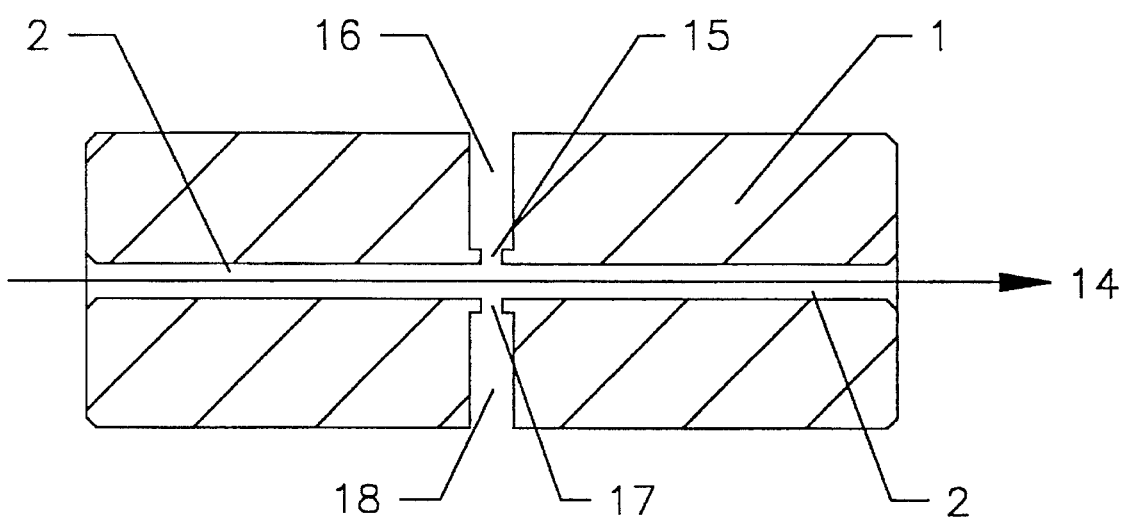
FIG. 3 shows an overview of the transverse structural modifications to the 927 or 217 flow cell for a preferred embodiment of the present invention.
Figure 4:
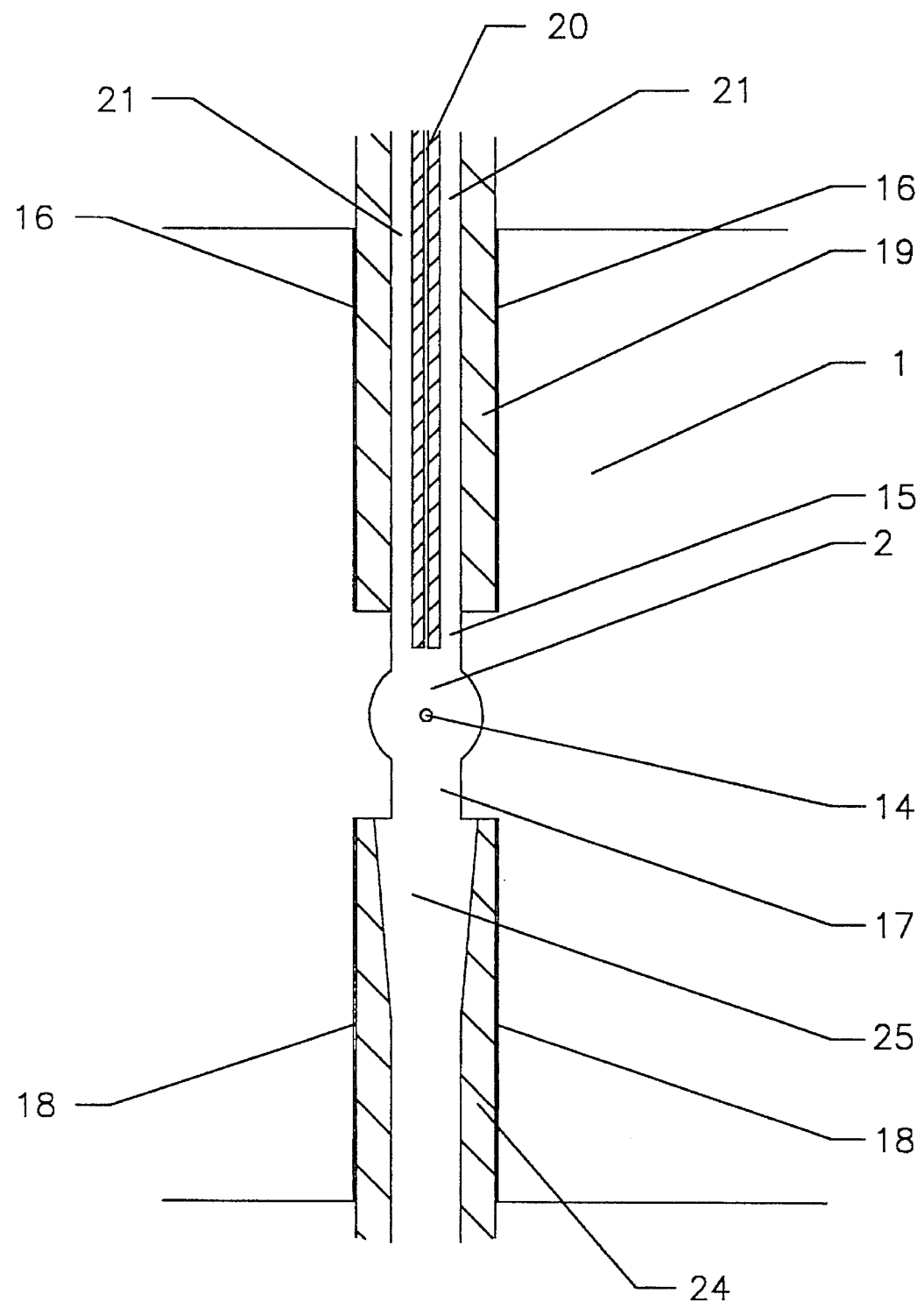
FIG. 4 shows a cross sectional view of a plane through the transverse holes of FIG. 3 and perpendicular to the axis of the main bore.

Because of the very small dimensions of the samples within the capillary, it remains an important task to maintain the glass/liquid interfaces through which the illuminating beam passes as far as possible from the scattering region where the light beam 14 strikes the sample. We have found that by modifying the 927 or 217 flow cell transverse to the bore 2 as shown in FIGS. 3 and 4, this requirement will be satisfied yet still permit implementation of the refractive properties of the 927 or 217 flow cell. Perpendicular to the cell bore 2 and through its center is drilled a transverse hole 15 with counterbore 16, from the top into which sleeve tubing containing the capillary is mounted, and continuing to hole 17 and counterbore 18 at the bottom through which the waste will exit the flow cell. Also shown in FIG. 4 is said sleeve tubing 19 butting up against the bottom of counterbore 16 and the capillary 20 centered in the sleeve about which will flow a fluid 21 creating a sheath flow about eluant leaving the capillary 20.

Figure 6:
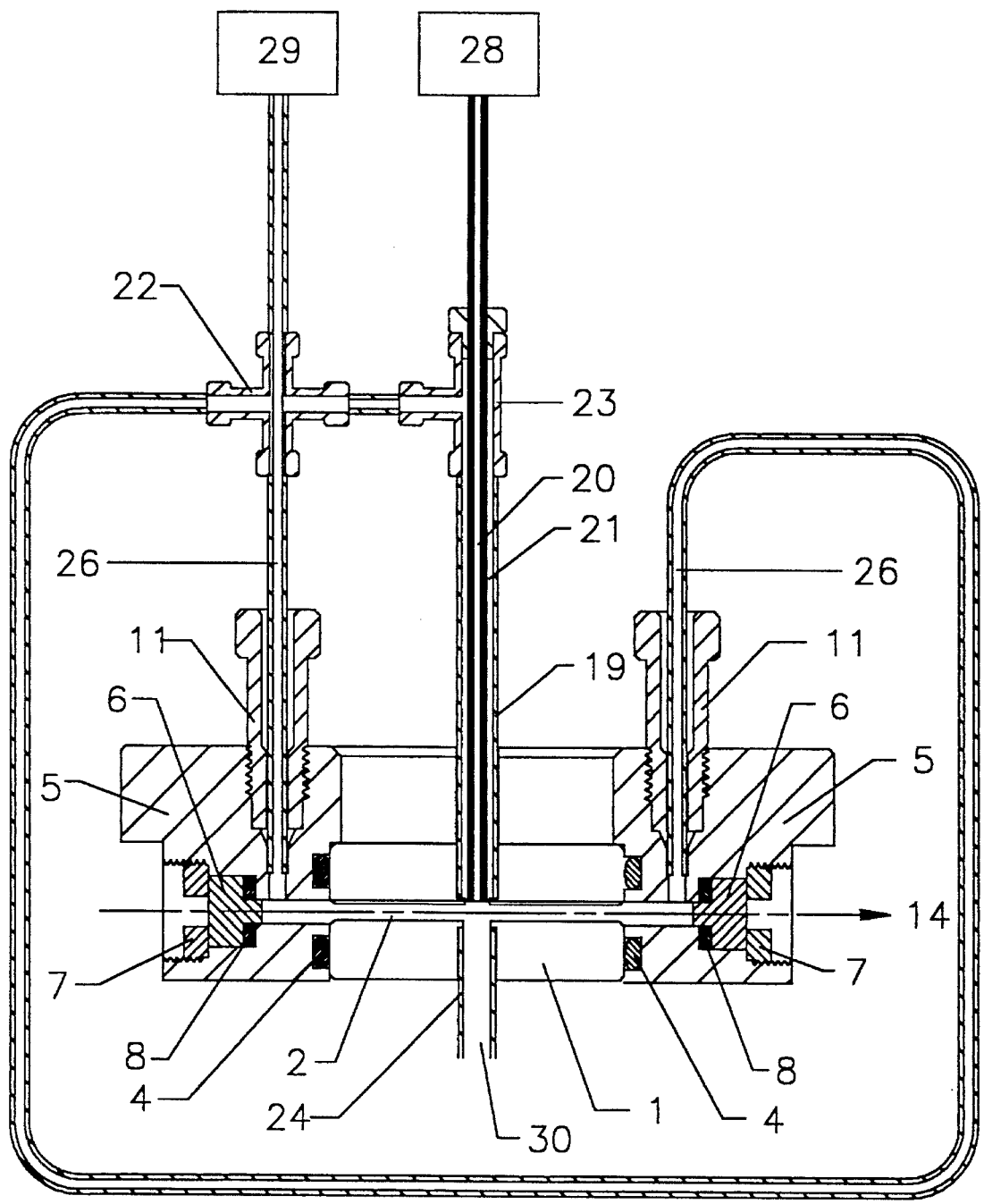
FIG. 6 shows details of the modified flow cell as interfaced to a CE system capillary following separation by CE.

The light beam 14 enters the flow cell through and parallel to the bore 2 after passing through a window 6 as indicated in FIG. 1. In order to maintain a good quality of sheath flow about the sample eluting from the capillary 20 it has been found that the sheath fluid 21 provided through the top hole 15 is insufficient. By introducing a symmetric horizontal flow from both sides of the eluting sample via the fittings 11 shown in FIG. 1, the integrity of the separated eluting sample is better maintained thereby. In a preferred embodiment of this invention, it has been found that the combined sheath flow created from the two sources at each of the two fittings 11 and the sheath fluid 21 will make up the final entraining sheath flow about the sample combined sheath flow, as it moves through the light beam 14. The velocity of the combined sheath flow which should be of approximately the same velocity as the eluting sample. This is best achieved by using a cross fitting 22 as shown in FIG. 6. By selecting the tubing lengths and inner diameters of the connections between this cross, two fittings 11 and capillary sheath flow tee fitting 23, the flow rates of all three sheath sources can be made approximately the same. As would be obvious to those skilled in the art of constructing sheath flows, the individual flows might well be changed and/or adjusted by the use of separate pumps, valves, or restrictors and may not be all the same for best operation. The two contributing side flows through fittings 11 provide another special benefit to the resulting sheath flow; they essentially eliminate any diffusion from the sheath entrained particles to the windows through which the light source beam enters or leaves the scattering region. By continually driving sample and contaminants towards the waste hole 17, the flows from fittings 11 help insure that the windows 6 are kept clear thereof. It is well known for most types of sheath flow containment that them will be present a small component of transverse diffusion from the entrained particles. Were it not for the transverse flow through fittings 11, the space between the windows 6 and the sheath flow from 21 alone would be stagnant permitting, thereby particles to diffuse into this dead flow region and remain. Eventually, such particles could adhere to the windows 6 contributing, thereby, to flare phenomena which in turn would affect the quality of the detected signals.

FIG. 5 and 6 shows details of the modified flow cell as attached to a capillary source 28 such as a CE instrument. Fluid for the capillary sheath flow 21 is provided through tee fitting 23 from pumped source 29. The capillary 20 is surrounded by sleeve tubing 19 inserted in counterbore 16. It should be mentioned that contributing elements of this sheath flow are distinct from those of the Crosland-Taylor design. Crosland-Taylor provided a sheath flow comprised of two sources at right angles to each other and combined in a region preceeding the observation cell through which the entrained sample flowed.

Although the Crosland-Taylor flow entrained the injected particle stream sufficiently for " . . . microscopial examination . . . ", it served no function to maintain the observation cell window area free of diffusing particulates. In the present invention, particulate-free streams flow from the window regions in a direction exactly opposite the direction that diffusing particles would move to contaminate said windows creating thereby flare at the interfaces through which the light source enters and leaves. Furthermore without the third source 21 of the resulting sheath stream, we have found that the two orthogonal flows originating at fittings 11 and intercepting the injected or capillary-provided particulates, will result in the formation of two eddies on either side of the entrained particulate sample.

The capillary 20 protrudes almost into the bore 2 through hole 15. A similar lower counterbore 18 is used to butt the outflow tubing 24 that has a slight concave outward shape 25 to facilitate flow into outflow opening 30. The intersection of the light beam 14 with the sheath flow entrained eluant 27 is also shown. The three contributions to the net sheath flow are indicated by arrows 26 and 21. An important feature of the assembly overview shown in FIG. 6 is that the capillary enclosing sheath tubing 19 be slightly adjustable transversely so that the eluant stream may be modified and caused thereby to be steerable with respect to the incident light beam. This fine tuning feature insures a more perfect intersection of the particle stream with the light beam. Alternatively, a centering fixture could be included inside the sleeve tubing 19 to center the capillary without appreciably disturbing the sheath flow.

Figure 7:
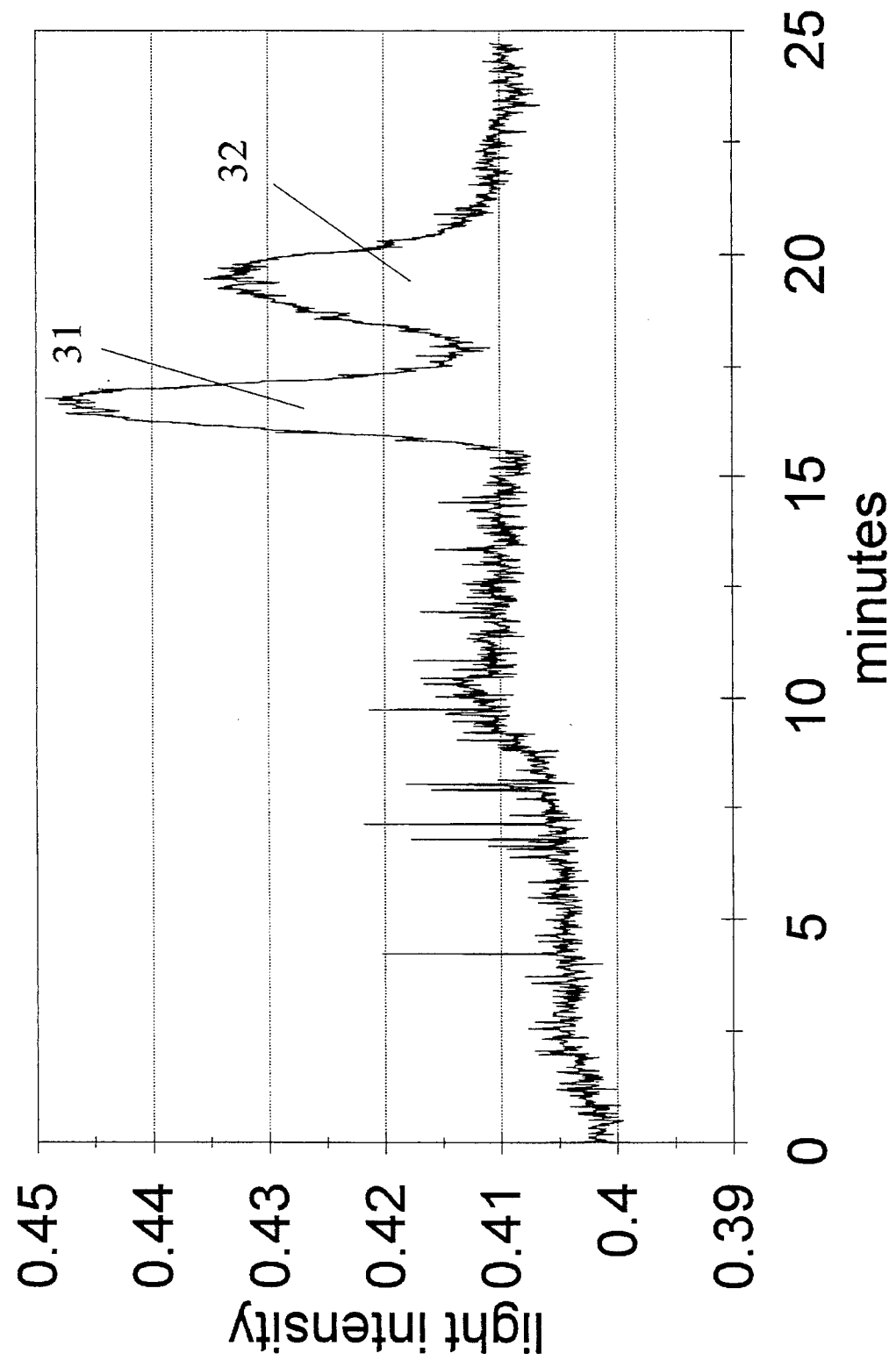
FIG. 7 shows 90° LS signals from two separated protein components of a CE sheath entrained eluant.
Figure 8:
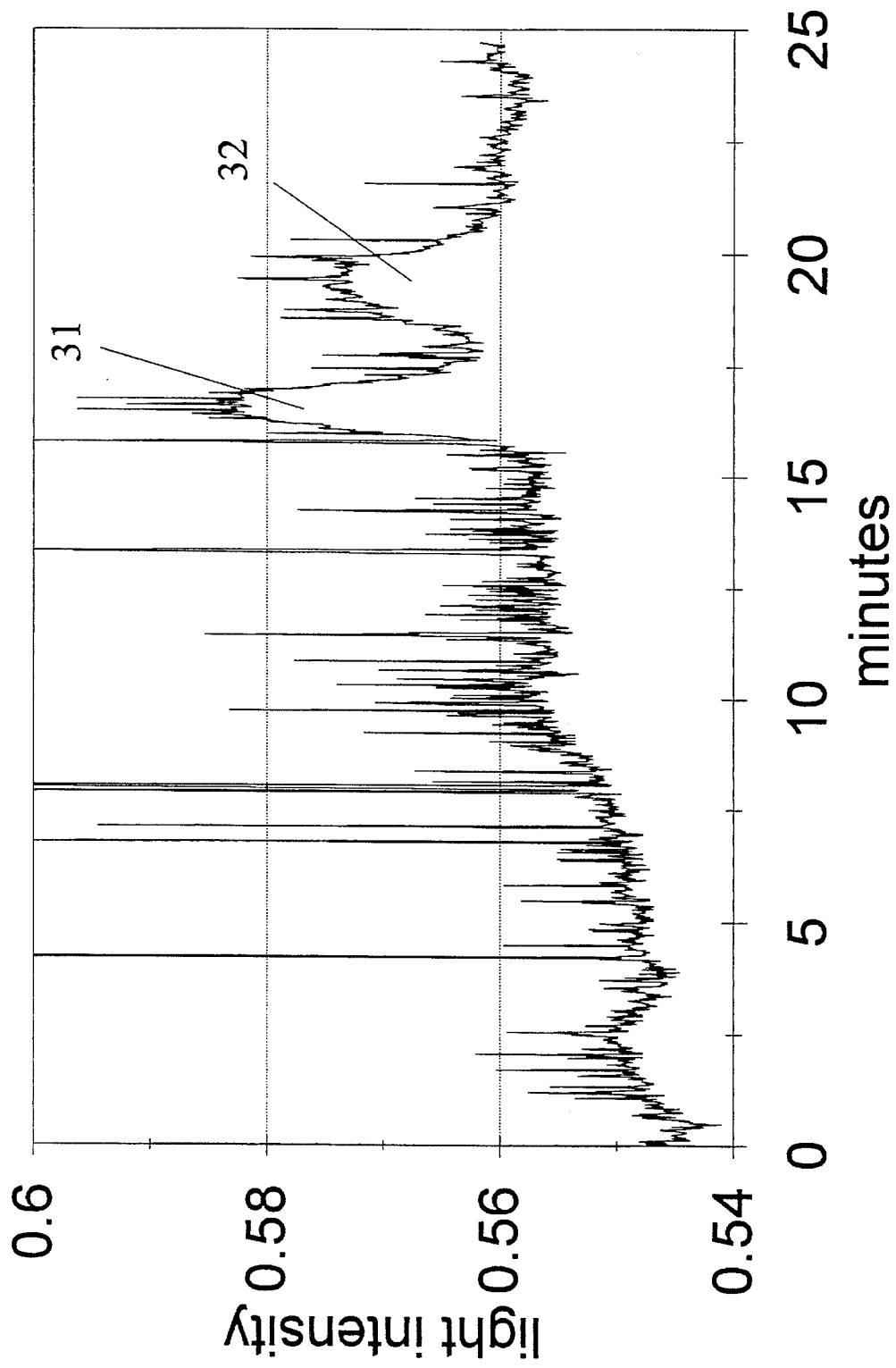
FIG. 8 shows the 37° LS signals from the same sheath entrained sample of FIG. 7.

FIG. 7 shows an early example of the light scattered at 90° from a sheath entrained eluant separated by CE using a modified 217 flow cell and a Model HP3D CE unit manufactured by Hewlett Packard. The two peaks 31 and 32 indicated correspond to two protein constituents of approximate molecular weights 17000 and 35000 gm/mole, respectively. FIG. 8 shows the scattering signals at 37° for the same eluant. Noise spikes are clearly visible which may be removed by various mathematical techniques, if required. As discussed earlier, had these same samples been diluted to fill the bore of the 217 cell and measurements made following conventional procedures, the signals could not have been detected above the baselines indicated.

The key elements of the modifications to the 217 flow cell that permit utilization of its refraction properties while maintaining the integrity of a separated sample entering through a capillary of diameter much smaller than the cell bore are, therefore:

a) a sheath flow surrounding the eluant from the print at which it leaves the capillary, maintaining thereby the eluant integrity;

b) the great spatial separation between the transparent interfaces through which the incident light beam enters and leaves the cell and the illuminated sheath entrained eluant;

c) the secondary flows contributing to the net sheath flow which prevent eluant diffusion onto the transparent interfaces through which the light beam enters and leaves the cell;

d) the use of a fine light beam such as produced by a laser to illuminate the sheath entrained eluant, said light beam having dimensions large enough to insure essentially uniform illumination on the eluting particles transverse to their direction of flow; and e) means by which the sheath entrained eluant stream may be adjusted so that it intersects the illuminating light beam and is centered in the sheath flow.

Figure 9:
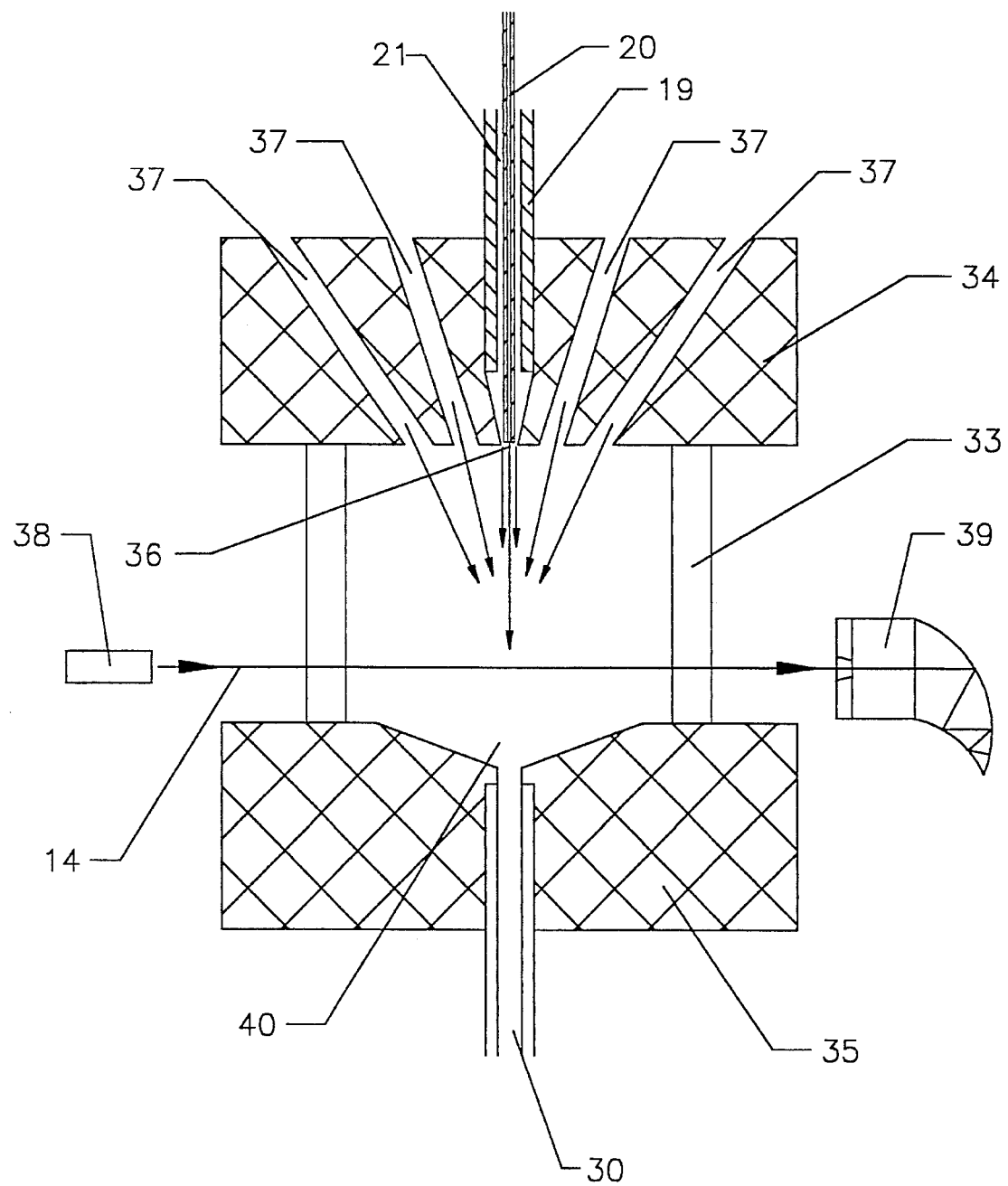
FIG. 9 shows a generalized structure for entraining particles within a fine sheath flow while, at the same time, permitting LS measurement with minimal stray light.

It should be evident that the modified 217 cell design may be generalized if the refraction properties of the cell are not required. These refraction properties permit the measurement of scattered light at small scattering angles while minimizing background stray light and flare. With a more conventional cylindrical geometry, smaller angle scattering is more difficult to obtain because of flare problems associated with the interface surfaces through which the light beam enters and leaves the scattering region. For very small molecules or particles, scattering measurements over a range of intermediate angles, say 30° to 110°, may be sufficient to derive mass and size information. Conventional flow cell structures, such as shown in the aforereferenced patent of Friedman et al., would be inappropriate for such measurements because of the extremely small radius of curvature of the cylindrical region containing the entrained particles. What is required is a very large radius of curvature cell with its associated large scattering volume, preferably with planar entrance and exit windows, at the center of which is the sheath flow entrained particle stream of very small transverse extent. The Crosland-Taylor structure is equally unacceptable for this purpose because of the inability of said flow structure to prevent diffusion to the windows through which the illuminating beam passes. In addition, the Crosland-Taylor design does not provide means for orienting/steering the entrained capillary stream. A useful alternative cell design is shown in FIG. 9. This arrangement provides a sheath entrained eluant at the time of entering the scattering chamber wherein it is further confined by means of secondary flows entering so as to intersect the main sheath flow downstream. FIG. 9 shows a preferred embodiment of such a cell.

In contrast to the conventional flow cell geometry of Friedman et al., the cell of FIG. 9 provides a large radius of curvature transparent containing structure such as a glass tube 33 with upper 34 and lower 35 end cap structures. The upper endcap provides the capillary 20 through which the fractionated sample enters the scattering cell 33. The scattering cell is surrounded by a plurality of detectors generally in the plane of the light beam, though some off-plane detectors may be required. The capillary is again centered in a larger tube 19 through which flows sheath fluid 21, the thus entrained sample entering the scattering region at opening 36. Secondary sources of sheath fluid enter the scattering cell through a plurality of openings 37 in said upper endcap which combine with sheath flow 21 to stabilize and confine further the sample as it passes through the light beam 14 on its way to the lower endcap 35 through the outflow opening 30. Note that initially, as they enter the transparent region through which the capillary eluant will pass, they contribute some components transverse to the eluant flow and are stabilizing thereto. In addition, these transverse flow contributions prevent the migration or diffusion of eluant contained particles that might otherwise reach the transparent containing structure, interfering thereby with the unimpeded passage of the illuminating light beam to the scattering particles within the eluant. The light beam source 38 whose beam 14 may enter a light trap 39 after leaving the scattering region. Because of the peripheral flows through openings 37, the effects of sample diffusion transverse to its direction of flow will be minimized and the interfaces through which the light beam passes will remain clean and the associated flare effects minimized. If the openings 37 are directed towards the center of the cell, they will contribute a horizontal component adjustably greater than any mean transverse diffusion velocity, further insuring thereby that windows 33 remain free of precipitates originating in the capillary 20. A concave bottom endcap region 40 will further contribute to the creation of sheath flow, about said capillary introduced particles, having small transverse/horizontal elements to overcome transverse diffusion.

The flow cell of Hershberger, et al. also has a relatively large outer boundary but does not incorporate the secondary flows discussed above. The Hershberger cell will therefore suffer from eventual coating of the windows by material trapped by the large dead flow volumes next to them. Stray light will increase due to scattering both from the contaminated windows and from particles trapped in the dead flow volumes. The Hershberger cell has two detection windows at 90° to the laser beam axis and is therefore not suitable for detection of light scattering at angles of less than about 50°.

There are obvious variations of the generalized flow structures described within this specification. Key to the success of any such configuration is the need to restrict the capillary eluant within transverse limits small compared to the distances to the interfaces through which the light beam enters and leaves the containing cell. The velocities of the primary and secondary constituents of the sheath flow must be capable of adjustment so that the entrained capillary eluant flow will maintain the separations present at the time of emergence from the capillary.

One obvious generalization would be the use of a gaseous fluid or vapor instead of a liquid for the eluant and sheath flows. Such as is common in separations performed with gas chromatography, or supercritical fluid chromatography where both gas and fluid may be present, represents an application where both liquid and gas sheath flows might be used.

Now wherein hereinbefore has been described the method and means by which an eluant from a capillary or other spatially confined region may be illuminated by a light beam and its light scattering properties detected without appreciable dilution, it will be obvious to those familiar with the art that there are many other obvious variations of this method and means which are included or implied by the descriptions thereof.

We claim:

1. A transparent right cylinder flow cell (1), with a bore (2) along a diameter perpendicular to the axis of the cylinder and two flattened ends (3), used in conjunction with an incident light beam (14) for detecting light scattered by particles eluting from a capillary (20), said light beam passing through and parallel with said bore (2) of said flow cell and intersecting said eluting particles perpendicular thereto, comprised of A) a hole (15) through which said capillary (20) elutes, said hole being transverse to and intersecting the center of said bore from above and continuing to a hole (17) below said bore; all flows exiting by said lower hole therethrough B) a primary sheath flow means (21) surrounding said capillary (20) and entraining particles eluting therefrom (27);

C) window (6) and sealing means (8) at each end of said bore through which said incident light beam may enter and exit, respectively, said bore; and D) flow source fittings (11) near each end of said bore to provide perpendicular inflow of fluid (26) from each end to pass through said bore symmetrically from respective end and toward said sheath entrained particles at said bore center, each said inflow intersecting said sheath perpendicularly thereto and both perpendicular inflows combining therewith to exit through said lower hole (17).

2. The modified flow cell of claim 1 where said capillary (20) and entraining particles eluting therefrom (27) is the output capillary of a capillary electrophoresis apparatus.

3. The modified flow cell of claim 1 where said capillary (20) and entraining particles eluting therefrom (27) is the output of a capillary hydrodynamic fractionation apparatus.

4. The modified flow cell of claim 1 where said capillary (20) and entraining particles eluting therefrom (27) is the output of a liquid chromatography column.

5. The modified flow cell of claim 1 where said capillary (20) and entraining particles eluting therefrom (27) is the output of a gas chromatography apparatus.

6. The modified flow cell of claim 1 where said capillary (20) and entraining particles eluting therefrom (27) is the output of a supercritical fluid chromatography apparatus.

7. The modified flow cell of claim 1 where said capillary is adjustable in the sheath tube by means of a movable sheath/capillary combination fitting.

8. The modified flow cell of claim 1 where said capillary is automatically centered by means of a centering device inside the sheath tube which presents a low cross-section to any sheath flow present.

9. The modified flow cell of claim 1 where said secondary sample-surrounding sheath flow, when present intercepts said primary sheath flow, when present, with all flows meeting near the center of said containment structure and exiting co-linearly down through said flow outlet means.

10. The modified flow cell of claim 1 where said primary sheath flow, when present, is created in a region prior to the region in which said secondary sheath flow, when present, originates.

11. A method for entraining, transporting and illuminating the eluant from a capillary within a transparent containment structure of cylindrical form to permit the subsequent measurement of light scattered by said eluant comprising the steps of a) surrounding said capillary with a concentric tube through which a liquid may flow parallel to the flow within the capillary creating thereby a primary sheath flow about said eluant;

b) flowing said sheath entrained sample perpendicularly to the center of a narrow bore lying along a diameter of said transparent containment structure;

c) impinging two opposing secondary flows, whose origins are respectively at each of the two ends of the bore, upon and transverse to said primary sheath entrained eluting sample to combine therewith and form an augmented secondary sheath flow about said eluant;

d) providing within said transparent containment structure windows at each end of said bore sufficiently distant from said eluant to permit, respectively, entrance into and exit out of said containment structure by a light beam that passes through said windows and said bore and which intersects said sheath entrained eluant; and e) providing an outlet means for said sheath entrained eluant to flow perpendicularly through the bore and leave said containment structure without stagnation or diffusion of said sheath entrained eluant toward said windows.

12. The method of claim 11 where said transparent structure is a right cylinder with a flattened surface at each end of said bore.

13. The method of claim 11 where said eluant is the output of a liquid chromatography column.

14. The method of claim 11 where said eluant is the output of an electrophoresis capillary.

15. The method of claim 11 where said eluant is the output of a capillary hydrodynamic fractionation apparatus capillary.

16. The method of claim 11 where said eluant is the output of a gas chromatograph.

17. The method of claim 11 where source of said light beam is a laser.

* * * * *